United States Patent
Rosenberg

(10) Patent No.: US 8,920,824 B2
(45) Date of Patent: Dec. 30, 2014

(54) PRETREATMENT OR POST EXPOSURE TREATMENT FOR EXPOSURE TO A TOXIC SUBSTANCE BY PULMONARY DELIVERY (INHALER) OF A BIOSCAVENGER

(71) Applicant: Yvonne Rosenberg, Washington, DC (US)

(72) Inventor: Yvonne Rosenberg, Washington, DC (US)

( * ) Notice: Subject to any disclaimer, the term of this patent is extended or adjusted under 35 U.S.C. 154(b) by 0 days.

(21) Appl. No.: 13/769,799

(22) Filed: Feb. 18, 2013

(65) Prior Publication Data
US 2013/0156749 A1  Jun. 20, 2013

Related U.S. Application Data

(63) Continuation of application No. 13/454,029, filed on Apr. 23, 2012, now abandoned, which is a continuation of application No. 11/128,997, filed on May 13, 2005, now Pat. No. 8,168,175, which is a continuation of application No. PCT/US03/36117, filed on Nov. 13, 2003.

(60) Provisional application No. 60/425,726, filed on Nov. 13, 2002.

(51) Int. Cl.
*A62D 3/00* (2006.01)
*A62D 3/02* (2007.01)
*A61K 38/46* (2006.01)
*A01N 25/00* (2006.01)
*A01N 25/32* (2006.01)
*A61K 31/215* (2006.01)
*A61K 45/06* (2006.01)
*A61K 9/00* (2006.01)
*A61K 31/66* (2006.01)

(52) U.S. Cl.
CPC ............... *A61K 9/007* (2013.01); *A61K 31/215* (2013.01); *Y10S 588/901* (2013.01); *A61K 45/06* (2013.01); *A61K 9/0078* (2013.01); *C12Y 301/01007* (2013.01); *A61K 31/66* (2013.01); *A61K 9/0075* (2013.01); *C12Y 301/01008* (2013.01); *A61K 38/465* (2013.01)
USPC ....... 424/406; 424/94.6; 424/405; 435/262.5; 588/300; 588/400; 588/401; 588/402; 588/405; 588/901

(58) Field of Classification Search
None
See application file for complete search history.

(56) References Cited

U.S. PATENT DOCUMENTS

| | | | |
|---|---|---|---|
| 6,207,703 B1* | 3/2001 | Ponikau | 514/460 |
| 8,168,175 B2* | 5/2012 | Rosenberg | 424/94.1 |
| 2003/0113902 A1* | 6/2003 | Gordon et al. | 435/262.5 |
| 2004/0147002 A1* | 7/2004 | Cohen et al. | 435/194 |

OTHER PUBLICATIONS

Nalivaeva et al., "Post-translational . . . model system," Proteomics 1:735-747, 2001.*
Doctor et al., "New approaches . . . nerve agents," pp. 191-214, 2001.*

* cited by examiner

*Primary Examiner* — Debbie K Ware
(74) *Attorney, Agent, or Firm* — MDIP LLC

(57) ABSTRACT

The present invention relates to a treatment by pulmonary delivery of a bioscavenger to animals as an effective antidote to prevent toxicity produced by exposure of an animal to nerve agents and other toxic substances.

21 Claims, No Drawings

PRETREATMENT OR POST EXPOSURE TREATMENT FOR EXPOSURE TO A TOXIC SUBSTANCE BY PULMONARY DELIVERY (INHALER) OF A BIOSCAVENGER

CROSS-REFERENCE TO RELATED APPLICATIONS

This application is related to U.S. provisional application Ser. No. 60/425,726 filed Nov. 13, 2002, the contents of which are incorporated herein by reference.

FIELD OF THE INVENTION

The present invention relates to a treatment by pulmonary delivery of bioscavengers to animals as an effective antidote to prevent toxicity produced by exposure of an animal to nerve agents and other toxic substances. In one embodiment, the disclosure relates to the delivery of functional bioscavenger cholinesterase molecules as a protective in vivo treatment against poisoning by nerve agents and drugs including but not limited to cocaine, heroin and succinylcholine.

BACKGROUND OF THE INVENTION

Exposure to organophosphates (OPs) in the form of nerve agents (e.g. sarin, soman and VX) and pesticides (e.g., paraoxon, parathion and malathion) may result in acute cholinergic effects by inhibition of acetylcholinesterase (AChE), permitting continuous firing of neurons and thereby producing toxicity, behavioral deficits and death. Of late, such agents pose an ever increasing military and civilian threat due to heightened terrorist activity. Traditional multi-drug treatment for poisoning by OPs consist of a combination of drugs such as carbamates (e.g. pyridostigmine), antimuscarinics, reactivators of inhibited AChE and anti-convulsants in postexposure modalities. These treatments, however, are far from optimal and do not prevent respiratory stress, tremors, convulsions and behavioral impairments. In recent years, exogenous administration of "self" native enzyme scavengers e.g. cholinesterases (ChE) have been successfully used in many species (mice, rats and monkeys) as safe and efficacious prophylactic and post exposure treatments due to their capacity to scavenge OPs in the blood and rapidly detoxify the active components before inhibition of the endogenous targets can occur. Such bioscavengers are shown to be highly stable, specific and efficient, to have long half-lives in homologous systems and capable of functioning under physiological conditions without producing immunological or other adverse side effects. In addition to nerve agents, certain bioscavengers can be also used to neutralize drugs such as cocaine, heroin and succinylcholine (a cause of apnea).

SUMMARY OF THE INVENTION

This present invention provides noninvasive and needleless methods for the inhalation delivery of a bioscavenger capable of rapidly ensuring entry of the bioscavenger into the blood so that (a) a real time response to assault by a toxic substance is accomplished, as e.g. in an incoming attack involving a nerve agent, and (b) first responders to civilian attacks can upgrade their protection between the time they get notification of a chemical incident and the time they arrive on the scene. The adaptability and portability of an inhaler also means that new modified forms of the scavenger molecules as well as the co-delivery of additional "enhancing" molecules can be supported in order to increase the scavenging capabilities with reduced treatment doses.

In one embodiment, the present invention describes a method for the pulmonary delivery of a native or recombinant bioscavenger for the in vivo detoxification/neutralization of organophosphates including nerve agents, pesticides, insecticides as well as drugs such as heroin, cocaine and succinyl choline. The bioscavenger is administered as a single or multiple dose prophylactic (preexposure) or therapeutic (post exposure) treatment.

In one embodiment, the present invention describes a method for the pulmonary delivery of native or recombinant butyrylcholinesterase for the in vivo detoxification/neutralization of organophosphates including nerve agents, pesticides, insecticides as well as drugs such as heroin, cocaine and succinyl choline. The butyrylcholinesterase is administered as a single or multiple dose preexposure or post exposure treatment.

Pursuant of the present invention, delivery of native and recombinant (r) BChE molecules, either in powder or liquid form by inhalation can be used for (i) Protection against chemical warfare agents in terrorist/battlefield situations; (ii) Clinical treatment of drug overdosing with cocaine, heroin; (iii) Alleviating life threatening conditions such as succinylcholine-induced apnea; (iv) neutralization or inactivation of toxic substances following pre or post exposure of first responder civilians and farmers to nerve agent, insecticides or pesticides. Succinylcholine is an exogenously administered drug which causes muscle relaxation and is given prior to surgery. This includes the muscles required for breathing. In people lacking BChE succinylcholine cannot be cleared, resulting in apnea (inability to breathe). This can be overcome by treatment with BChE.

In one embodiment, the invention provides a method for the treatment of an animal for the detoxification or neutralization of a toxic substance which comprises administering to said animal a bioscavenger molecule that prevents the toxic effects of said toxic substance in the animal, wherein said bioscavenger molecule is administered to said animal by an inhalation process. In a preferred embodiment, the animal is a human.

In one embodiment, the bioscavenger is administered by inhalation delivery of a dose between 1 and 10 mg per Kg of body weight of said animal.

In another embodiment, the bioscavenger is administered by inhalation delivery of a dose, of bioscavenger that is sufficient to prevent the toxic effects of 2 LD50 of, e.g., a nerve agent In another embodiment, the invention provides single or multiple dose preexposure administration of said bioscavenger. In another embodiment, post exposure treatment with a bioscavenger is given in combination with an oxime that reactivates said bioscavenger. The bioscavenger can be a native blood-derived product or a recombinant molecule in either a monomeric or tetrameric form.

In a preferred embodiment, said recombinant molecules are glycosylated in vitro to mimic the structure and function of the native molecule.

DETAILED DESCRIPTION OF THE INVENTION

In general terms, the use of an effective pretreatment using nerve agent scavenger such as BChE could preclude the necessity of carrying or wearing protective clothing or masks because high levels of the scavenger in the blood would neutralize and thus protect against nerve agents in the absence of protective equipment. This feature is important to soldiers in the Army in battlefield conditions and to the Marines who guard Embassies worldwide and who are unable to don protective clothing. In terms of non-military personnel, treatment with bioscavengers is important to any civilian first responders who must enter an exposed area, those exposed to environmental toxins in insecticides and those suffering drug overdose and apnea.

Based on availability, broad spectrum efficacy and safety, the cholinesterase, butyrylcholinesterase (BChE) is the only pan scavenger candidate sufficiently developed for human treatment and is the preferred bioscavenger of the present invention. A pan scavenger is one which works on multiple nerve agent targets. Since cholinesterases are stoichiometric inhibitors (one molecule of enzyme neutralizing one molecule of nerve agent), humans require a large dose of scavenger e.g. 150-200 mg (~3 mg/Kg) of BChE, in order to protect against an exposure of 2 $LD_{50}$ of nerve agent. While bioscavengers can be administered via IM, IV, transdermally or by pulmonary routes prior to exposure, an inhaler is by far the simplest, safest and most efficient means of delivery. Traditionally, bioscavenger drugs/treatments have been administered orally or via the intramuscular route using autoinjectors. Major limitations to the use of the commonly used modes of delivery is the inability to deliver large molecules (transdermal patches), a long delay in reaching blood peak levels of bioscavenger activity, major soreness at the injection sites and potential infections (intramuscular) and the impracticality in battlefield/high risk conditions of intravenous injections. By contrast, pulmonary administration of peptides and proteins can be expected to lead to higher and more rapid rates of systemic absorption than other non-invasive routes because the alveolar epithelium where absorption takes place is thin and has a large surface area (~1,500 sq ft). Pulmonary delivery is performed via introduction of the bioscavenger through the nose or mouth via inhaler or nebulizer. In a preferred embodiment, delivery is by mouth with an inhaler.

A critical feature required of any effective nerve agent scavenger is that as a pre or post exposure treatment, it must (i) have good stability, that is, circulate in the blood at high concentrations for prolonged periods and (ii) in emergency conditions, the enzyme must reach peak levels as quickly as possible. To prevent toxicity, nerve agents must be reduced to a level below their median lethal dose within one blood circulation time.

Scavenger enzymes are usually complex glycoproteins and stability of the molecules is greatly influenced by glycosylation profiles, efficiency of folding and multimerization. In this regard, unlike the native blood-derived forms, recombinant prophylactic/therapeutic molecules produced by genetic engineering e.g. BChE, exhibit microheterogeneity in the sugar residues which negatively impacts on the rate of clearance in vivo and may limit their use as human treatments. In the present invention, this deficiency is overcome by in vitro glycosylation methodologies which complete or correct sugar profiles of the "incorrectly" expressed recombinant protein and produce a form of the scavenger which mimics the native form in structure and pharmacokinetic function. As therapeutic human treatments, "remodeled sialyted" recombinant molecules, in contrast to native plasma-derived molecules, should not suffer from batch to batch variability or from potential safety issues associated with contaminating infectious agents (HIV-1, hepatitis, prions, etc.)

It is understood that the present invention is not limited to the particular methodology, protocols, and reagents, etc., described herein, as these may be substituted or altered without deviating from the invention, and will be understood by one of ordinary skill in the art. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Prevention of toxic effects of a toxic substance "in" an animal is meant to include any toxic effects that may manifest "on" the animal, as in the case for toxic effects on the skin or other exposed surface. Preferred methods, devices, and materials are described, although any methods and materials similar or equivalent to those described herein can be used in the practice or testing of the present invention. All references cited herein are incorporated by reference herein in their entirety.

In a preferred embodiment, the invention provides methods for the delivery of a homologous bioscavenger. In the treatment of humans, an example of a homologous bioscavenger would be the human BChE product, which can be blood derived or recombinant. In the absence of an available homologous bioscavenger, a single treatment with heterologous can be performed. If repeated administrations are required as in long term pre-exposure protection, then it must be homologous because the body would make an immune response to a foreign protein and eliminate the protein from the body.

The bioscavenger can be administered in a powder or liquid droplet form.

It is one object of the present invention to deliver a variety of scavenger molecules including but not limited to native 'self' enzyme molecules including, but not limited to, (butyrylcholinesterase (BChE), acetylcholinesterase (AChE)), carboxylesterase (CaE), paraoxonase, and bacterial enzymes such as organophosphate hydrolases (OPH), organophosphorous acid anhydride hydrolases (OPAA) and parathion hydrolase. For optimal efficiency, native molecules must be homologous with the recipients (Example 3). Life Sciences. Vol 72, p125 2002.

It is another object of the present invention to deliver scavenger molecules that have been successfully used as a safe and efficacious treatments to prevent poisoning by organophosphate (OP) compounds in the form of nerve agents including but not limited to organophosphates such as sarin (O-isopropyl-methylphosphonofluoridate), VX (ethyl-S-2-diisopropylaminoethyl-phosphano-thiolate), MEPQ (7-(Methylethoxyphosphinyloxy)-1-methylquinon-linium iodide), soman (pinacolylmethl-phosphonofluoridate), DFP=diisopylfluorophosphate paraoxon, malathion and parathion.

In one preferred embodiment, the bioscavenger is administered as a tetramer. In another embodiment, the bioscavenger is administered as a monomer. In some embodiments, the bioscavenger is a recombinant molecule. The bioscavenger molecule can be a recombinant molecule produced in vitro in mammalian or insect cells, or in transgenic plants or livestock.

In one embodiment, the invention provides a method of inhalation delivery of an altered bioscavenger which comprises a mutation with increased bioscavenging efficacy, for example as in E197Q BChE or E202Q AChE mutations. In another embodiment, the invention contemplates the post-exposure co-administration of the bioscavenger with an oxime which reactivates said bioscavenger. In some preferred embodiments, the oxime is selected from the group consisting of 2-PAM, HI6, toxogonin, TMB4.

The present invention provides an efficient, highly manageable and user-friendly means of delivery by inhalation (puffer) of bioscavenger molecules e.g. BChE, AChE in sufficient amounts required for protection against toxicity by nerve agents, insecticides and drugs. In the case of a stoichiometric (i.e., "BChE-like") bioscavenger alone, ~150-200 mg (~3 mg/Kg) is required to protect against an exposure of 2 $LD_{50}$ of nerve agent.

The methods disclosed herein encompass the use of inhalers to administer either powder or liquid forms of the bioscavenger, depending on the chemical properties of the candidate molecules (see Example 1). In one preferred embodiment, the bioscavenger is administered prophylactically, i.e., over a period of several weeks prior to any anticipated or possible exposure to the toxic agent. It is presently contemplated that a preferred dosage is delivered at a rate of ~10 puffs from a powder inhaler (~15 mg/puff of BChE) and that this dosage will initially protect against high levels of toxin exposure within 30 minutes. In a preferred embodiment, the treatment is repeated about 10 times on the first day, with maintenance puffs thereafter sufficient to provide protection.

In another embodiment, the invention provides methods of an initial administration of a bioscavenger rapidly across the pulmonary epithelium, as in the case of an impending (i.e, within 30-60 minutes) exposure to the toxic substance. In this embodiment, a truncated monomer bioscavenger molecule is administered so that the bioscavenger is more rapidly enters the blood.

It is one object of the present invention to develop an adaptable, noninvasive and needleless delivery system capable of rapidly ensuring entry of the bioscavenger into the blood so that (a) a real time response to an incoming attack would not be unreasonable, (b) civilian first responders could upgrade their protection between the time they get notification of a chemical incident and the time they arrive on the scene and (c) an injured soldier/victim can easily receive passive bioscavenger delivered by an another soldier/associate.

As a receptor or soluble receptor, the bioscavenger agent binds, sequesters, and clears the toxin as a complex from the body. As an enzyme, the agent binds, inactivates by hydrolytic or non-hydrolytic processes, resulting in toxins that are no longer harmful to mammalian tissues and/or are removed more rapidly from the host. Inactivation can occur, but is not limited to enzymatic cleavage, blocking of reactive moieties, masking of active site(s), sequestering to certain tissues, and/or clearance of the toxin as a bound or unbound complex.

It is another object of the present invention to deliver scavenger molecules that have been successfully used as a safe and efficacious anti-toxicants of nerve agents as both pre-exposure and post-exposure treatments.

It is another object of the present invention to deliver scavenger molecules that have been successfully used as a safe and efficacious post-exposure treatment to overcome drug overdosing such as cocaine and heroin.

It is another object of the present invention to deliver scavenger molecules that have been successfully used as a safe and efficacious post-exposure treatment to prevent apnea induced by the muscle relaxant succinylcholine.

Transpulmonary administration of peptides and proteins can be expected to lead to higher rates of systemic, absorption because of a large surface area (~1,500 sq ft). However, transpulmonary administration of high molecular weight compounds is almost always incomplete, because of absorption barriers in the alveolar epithelium. Permeation enhancers can increase the bioavailability of inhaled peptides and proteins in the blood by for example, increasing the paracellular permeability through tight junctions, a mechanism that depends on Ca++ channels.

In one embodiment of the present invention, protection against agent or drug toxicity is achieved using pulmonary delivery of any form of the scavengers in combination with permeation enhancers including but not limited to oleic acid, dimethyl-b-cyclodextrin and citric acid and polyethylene glycol (PEGylation).

The methods disclosed herein encompass the delivery of homologous recombinant bioscavenger molecules. The scavenger genes in question are cloned into the appropriate mammalian or insect cell expression vector (Example 4) or plant expression vector (Example 5). It is contemplated in the present invention that a transgenic construct of interest can be delivered to mammalian or plant cells by viral-mediated or non-viral mediated means. Recombinant virus vectors utilized in the present invention include, but are not limited to (I) retroviral vectors, including but not limited to vectors derived from a Moloney murine leukemia virus (MoMLV) or a myeloproliferative sarcoma virus (MPSV) (ii) adenovirus vectors (iii) adeno-associated vectors (iv) herpes simplex virus vectors (v) SV40 vectors (vi) polyoma virus vectors (vii) papilloma virus vectors; (viii) picornavirus vectors; and, (ix) vaccinia virus vectors. Depending on the virus vector system chosen, techniques available to the skilled artisan are utilized to infect the target cell of choice with the recombinant virus vector.

In some embodiments, these scavenger molecules are highly active complex tetrameric, glycoproteins e.g., BChE produced by the co-expression Of a peptide containing a proline-rich attachment domain (PRAD) in the expressing cells with the cholinesterase gene (Example 7). Alternatively, PRAD protein can be added in vitro to monomeric and dimeric forms of the scavenger molecules to effect tetramerization.

The methods disclosed herein encompasses methods for production of recombinant bioscavenger molecules in transgenic plants (Example 5). a mammalian cell system in vitro e.g. CHO (Example 6) as well as in the breast milk of transgenic livestock e.g. pigs, cattle and sheep.

In one preferred embodiment, the methods disclosed herein encompass a device for the delivery of homologous native (blood derived) BChE molecules that are purified, where appropriate, by procainamide and DEAE chromatography and administered alone or in combination with other molecules. In one embodiment, these scavenger molecule are complex tetrameric, glycoproteins such as butyrlcholinesterase (EC3.1.1.8 acylcholine achydrolase, pseudocholin-esterase, non-specific cholinesterase), a serine esterase (MW=345,000) comprised of four identical subunits containing 574 amino acids and held together by non-covalent bonds and contains 36 carbohydrate chains (23.9% by weight).

In addition to tetrameric molecules, monomeric BChE may be generated by inserting a stop codon at G534. Thus the mutant monomeric molecule produced lacks the 41 C-terminal residues and thus the functional tetramerization domain required for tetramer formation and in vivo stability (Example 8). The monomer has several advantages despite the fact that its stability in plasma is very poor. In addition to the >8-fold increase in activity per ml of CHO supernatant, a monomer may be able to more rapidly cross the blood-brain barrier and exhibit much higher bioavailability in the plasma following delivery via inhalers than the larger tetrameric molecules. In one embodiment, monomeric molecules, despite being ineffective in maintaining long term protection compared to the highly stable tetramers, may be highly efficacious in emergency situations that require real time responses and rapid treatment or booster administrations.

As a complex recombinant glycoprotein, a scavenger may require additional post-translational modifications to enable the agent to provide the necessary disabling function(s) similar to the native protein. Such glycoproteins are often produced with either incomplete or wrong sugar profiles compared to their plasma derived counterparts. For example: 1) The lack of a functional a,2,6-sialyltransferase (ST) gene in CHO cells 2). The presence of xylosidayed- and fucosylated-type sugar chains in many plant-derived glycoproteins and the absence of sialic acid in plants 3). The presence of galactosyl transferases in pigs resulting in the potential surface expression of a, 1.3 galactose, which is not normally found in humans. Several approaches that are available to overcome these innate deficiencies have either involved exposing recombinant proteins in vitro to enzymes such as exoglycosidases and sialyltransferases (Example 9) or introducing liver-derived enzyme beta-galactoside alpha-2,6-sialyltransferase cDNA by gene transfer into those cells producing the recombinant protein. The in vitro incorporation of sialic acid into recombinant proteins (developed specifically to allow efficient sialic acid capping of beta-galactose-exposed termini) has been highly successful. Such findings are in agreement with data showing that liver (the in vivo source of many of these highly sialylated glycoproteins) contain sialyltransferase, involved in the sialylation of O-glycosidically linked carbohydrate chains on serum glycoproteins. The in vitro glycosylation methodology utilized to modify the recombinant bioscavenger molecule can include, but is not limited to, glycosylation where the recombinant protein preparation is incubated with appropriate enzymes in solution or coupled to a solid support. These enzymes include but are not limited to, glycosltransferases, such as sialtransferases, galactotransferases, and fucosyltransferases.

In one preferred embodiment, following pulmonary delivery, improved pharmacokinetic profiles (stability) and manufacturing efficiencies of tetrameric and monomeric scavenger molecules, either wild type or mutant, produced in the various expression systems is achieved following in vitro sialylation of the recombinant glycoproteins to "correct" the microheterogeneity in their glycosylation profiles.

The rate of detoxification of an OP by a bioscavenger enzyme molecule is determined by three parameters: (I) the rate of inhibition of the enzyme by the OP (ii) the rate of aging of the OP-inhibited enzyme and (iii) the rate of reactivation of the enzyme by oximes. Following interaction of the OP with the scavenger enzyme, the latter may become immediately inhibited or undergo spontaneous or oxime-induced reactivation. In the latter case, the reaction of oxime nucleophile with the phosphonylated enzyme leads to displacement of the phosphonyl group and restoration of normal activity. In one embodiment of the present invention bioscavenger inhalation treatments can be co-administered post exposure with specific oxime molecules which can reactivate the enzyme scavenger and thus reducing the amount of scavenger required (Example 10). Such oxime molecules include but are not limited to 2-PAM, HI6, toxogonin, TMB4. This is particularly important, since many potent enzyme scavengers are stoichiometric inhibitors and require large amount of protein for protection (150-200 mg BChE per adult). In one embodiment the present invention provides mutant BChE clones (e.g. E197Q BChE or E202Q AChE) with a slower rate of aging and thus potentially superior scavenging capability that are delivered by inhalation as another means of reducing the amount of enzyme required for protection. In one embodiment of the present invention, a combination of mutant BChE plus oxime is delivered post-exposure via the lungs to further enhance the scavenging efficacy of nerve agent antidotes.

In general, the process of inhalation is meant to encompass the concept of delivery of a substance to the blood via the lungs, wherein delivery takes place across the pulmonary epithelium of an animal. Inhalation can be via mouth, nose or intratracheal. Most inhalers use the mouth, which is a preferred method of inhalation in the present invention. Delivery by inhalation can be by means of an inhaler or nebulizer, many of Which are known to those of ordinary skill in the art. See, e.g., U.S. Pat. No. 6,595,202 the contents of which are incorporated by reference herein. Delivery by an inhaler is preferred. Delivery can be an active process of the animal to which the bioscavenger is administered or via a passive means. Some pulmonary delivery techniques rely on the inhalation of a pharmaceutical formulation by the patient so that the active drug within the dispersion can reach the distal (alveolar) regions of the lung. A variety of aerosolization systems have been proposed to disperse pharmaceutical formulations. For example, U.S. Pat. Nos. 5,785,049 and 5,740,794, the disclosures of which are herein incorporated by reference, describe exemplary powder dispersion devices which utilize a compressed gas to aerosolize a powder. Other types of aerosolization systems include those which typically have a drug that is stored in a propellant, nebulizers which aerosolize liquids using a compressed gas, and the like.

Many of the advantages of administering BChE by inhalation include the following: non-invasive; user friendly; suitable for repeated administration; can deliver small and large molecules/proteins and peptides; large absorptive surface area for delivery; highly permeable single cell membrane; and rapid (depending on compound).

The following examples further illustrate experiments that have demonstrated reduction to practice and utility of selected preferred embodiments of the present invention, although they are in no way a limitation of the teachings or disclosure of the present invention as set forth herein.

Other objectives, features and advantages of the present invention will become apparent from the following specific examples. The specific examples, while indicating specific embodiments of the invention, are provided by way of illustration only. Accordingly, the present invention also includes those various changes and modifications Within the spirit and scope of the invention that may become apparent to those skilled in the art from this detailed description.

EXAMPLES

Example 1

Below are the relevant properties of complex molecules which currently determine whether liquid or powder inhalers are chosen:
Liquid
1. Inhalers are expensive
2. Most proteins are made in a liquid form, thus lower development costs for some molecules
3. Must be kept frozen or cold. RT prior to use
4. 50 ul/puff (at 20 mg/ml=1 mg puff)
5. ~65% to get to the lung=~650 ug
6. Require >200 puffs for 150-200 mg
7. Bioavailability (lung to blood, depending on the compound)

Powder
1. Inhalers are not as expensive
2. Must produce a powder. May be difficult and less efficient to make a large molecule into 1-4μ particles
3. High stability as a powder at RT
4. Up to 25-30 mg/puff
5. ~50% gets to the lungs=~15 mg
6. Require 10-15 puffs for 150-200 mg
7. Bioavailability (lung to blood, depending on the compound)

Example 2

The Importance of Using Homologous Scavenger Molecules in vivo

As bioscavengers, molecules must exhibit good bioavailability and good stability (high mean retention times, MRT) in blood following administration. Work in monkeys using purified native macaque BChE (MaBChE), has shown that homologous BChE has a very long retention time in blood (MRT=225+/−19 hours following a single i.v. injection) compared to current treatments and induces no antibody responses. By comparison, an injection of heterologous human (Hu)BChE into monkeys results in a short retention time (MRT 33.7+/−2/9 hours) and induces antibodies. In addition, the administration of 7,000 U (10 mg) of purified homologous macaque BChE into macaques is known to protect against 2.1 LD50' of VX and 3.~LD50 soman with no induction of anti-BChE antibody and no adverse toxicological effects. The development of a human treatment require evidence in monkeys of similar stability following pulmonary delivery. Life Sciences. Vol 72, p125 2002.

Example 3

The Effect of Absorption Enhancers on the Bioavailability of Bioscavengers in the Blood Following Pulmonary Delivery Oleic acid, dimethyl-b-cyclodextrin and citric acid are initially tested at different concentrations. 1,500-2,000 units of MaBChE are mixed with 50 or 250 ug of the different enhancers and the enzyme activity (bioavailability) in the blood is assessed at various times following intracheal administration into the mid lung.

Example 4

Cloning of MaBChE Gene in Mammalian Cell Expression Vector

For the production of rMaBChE in mammalian or insect cells, plants, transgenic animals and/or insects, the BChE gene from liver of macaques obtained from National Primate Research Center has been cloned. Total RNA was isolated from the liver and cDNA was synthesized by reverse transcriptase with oligo dT as primer. The synthesized DNA oligonucleotide primers used for the amplification of MaBChE gene from the cDNA were based on the human BChE sequence.

First the MaBChE gene was PCR amplified in two fragments, 5' and 3' fragments using PfuTurbo DNA Polymerase (Stratagene), and the amplified fragments were cloned into pCRH vector (Invitrogen). The 540 fragment was amplified with a pair of primers, O-Pro#11 and Pro#5, and the 3' fragment with O-Pro#4 and Pro#12. The resulting vectors containing the nucleotide sequences encoding $NH_2$-terminal and COOH-terminal fragments of MaBChE were digested with appropriate restriction enzymes and cloned into pcDNA3.1 (Invitrogen) to form a single MaBChE reading frame (pcDNA3.1-MaBChE). The genes cloned in pcDNA3.1 are expressed under the control of CMV promoter and the cells transfected with the vector are to be selected with G418. The nucleotide sequence of macaque BChE gene in the constructed vectors was confirmed by commercial sequencing.

Example 5

Cloning of MaBChE Gene in Plant Expression Vector and Enzyme Production

The production of MaBChE in plant or plant cells requires a plant-specific expression vector. For the optimal activity of the recombinant BChE, after production in plant, the protein is chemically glycosylated in the pattern mimics the pattern of endogenous glycosylation. When the proteins are expressed in plant via secretion pathway, they are heavily glycosylated in a plant specific manner which is problematic to remove for the chemical gycosylation. One means to prevent plant specific glycosylation is to design a vector which expresses the transgene in the endoplasmic reticulum and then complete glycosylation in vitro.

For the plant expression vector construct, one useful vector is the pTRAkt plant vector. The nucleotide gene sequence encoding mature MaBChE is PCR amplified utilizing Pfu-Turbo DNA Polymerase from a previously constructed plasmid vector, pcDNA3.1-MaBChE, with a pair of primers containing appropriate restriction enzyme sequences. The resulting about 1.8 kb amplified fragment is cloned into an intermediate pCRII vector. The nucleotide sequence of the cloned gene in pCRII vector is sequenced by commercial DNA sequencing. The MaBChE gene is excised from the pCRII vector with appropriate restriction enzymes and cloned into pTRAkt.

*Agrobacterium*-Mediated Transient Expression System and Plant Transformation

Agrobacteria is transformed with each of the plant expression vectors by electroporation. Recombinant Agrobacteria harboring MaBChE gene is coinfiltrated with the Agrobacteria harboring PRAD fragment into tobacco leaves by vacuum application. After infiltration, leaves are incubated adaxial side down, on wetted paper in sealed trays at 23° C. with a 16 h photoperiod. After 60 h, leaves are frozen in liquid nitrogen and stored at 80° C. until analyzed. Transient expression by agro-infiltration of tobacco leaves is highly efficient with accumulation levels being similar to those found in transgenic plants. Stable proteins yields up to 20-40 mg/kg fresh plant material have been obtained. For plant transformation, either tobacco leaf disks or YT-2 suspension cells are co-cultivated with recombinant agrobacteria, placed on selective media and regenerated to intact plant or further cultivated as suspension cells.

Protoplast Preparation

Protoplasts of suspension cells are isolated enzymatically using Cellulase and Pectyolase. The cells are incubated in the enzyme solution, filtered from cellular debris and then washed with buffer. Protoplasts are resuspended in a medium that favors elongative growth and cultured in the dark.

Extraction of Proteins from Infiltrated Leaves.

For the extraction of transiently expressed recombinant proteins infiltrated leaves are ground in liquid nitrogen to a fine powder with a mortar and pestle. Soluble protein is extracted with extraction buffer, cell debris is removed by two rounds of centrifugation, and the supernatant is used for expression analyses and further protein purification by affinity chromatography or sucrose gradient.

Purification of Protein Extracts from Infiltrated Leaves by Affinity Chromatography Soluble protein is extracted with extraction buffer, cell debris is removed by two rounds of centrifugation. A Ni-NTA column is equilibrated with binding buffer, and leaf extract is applied to the column at a constant flow rate. After sample application, the column is washed with binding buffer. Non-specifically bound proteins are removed with binding buffer containing 25 mM imidazole. His6-tagged gp120 is eluted by using binding buffer containing 250 mM imidazole.

Agrobacterium-Mediated Transient Expression Systems

Agrobacteria is transformed with each of the plant expression vectors by electroporation. Recombinant Agrobacteria is infiltrated into tobacco leaves by vacuum application. After infiltration, leaves is incubated adaxial side down, on wetted paper in sealed trays at 23° C. with a 16 h photoperiod. After 60 h, leaves are frozen in liquid nitrogen and stored at 80° C. until analyzed. For transient expression in tobacco suspension cultures, cells are co-cultivated with recombinant Agrobacteria on agar plates first, then transferred to liquid media and incubated for another two days. After harvesting the cells can be frozen and stored until further processed and analyzed.

Purification of Protein Extracts from Infiltrated Leaves by Affinity Chromatography Soluble protein is extracted with extraction buffer, cell debris is removed by two rounds of centrifugation. A Ni-NTA column is equilibrated with binding buffer, and leaf extract is applied to the column at a constant flow rate. After sample application, the column is washed with binding buffer. Non-specifically bound proteins is removed with binding buffer containing 25 mM imidazole. Tetrameric MaBChE is eluted by using binding buffer containing 250 mM imidazole.

Example 6

MaBChE Production in CHO-K1 Cells

Establishment of CHO cells that continuously produces and expresses primate (monkey or human) BChE demonstrates the principle of this invention. CHO cells were used that were stably transduced with a CMV or retroviral vector in which the BChE gene is driven by the long-terminal repeat regulatory region. For the production of MaBChE, CHO-K1 cells were transfected with pcDNA3.1-MaBChE vector using LIPOFECTAMINE PLUS reagent (Invitrogen) by the manufacture's procedure. Two days after transfection, G418 sulfate was added to the cell at the concentration of 400 mg/liter for the transfected cells. After 2 weeks selection, single cell colonies were prepared by limiting dilution for the isolation of cells expressing high level of MaBChE. When cells reached near confluence, the cell media was changed to fresh media and the cells were allowed to secrete MaBChE for 2 days. The 2-day media was collected and the BChE activity measured. The BChE expressed was tested to be biologically active. Out of 20 single cell-derived transfected colonies, 3 colonies showed higher than 0.2 unit/ml.

These expressing cells were then adapted to grow in suspension in CHO-S-SFM (serum-free media). High cell densities, typically $2.0\times10^6$ cells/ml were obtained from spinner flask cultures. Partial purification of BChE from CHO cell cultured media revealed that the level of impurities in SFM was significantly lower than the serum-supplemented DMEM. This suggests that additional steps need not be employed in the purification of butyrlcholinesterase from SFM. This would result in a reduction of the operating time by 50 h and boost the recovery yield of BChE to 75%.

To confirm the existence of transgene in the cells expressing high level of MaBChE, genomic DNA was isolated from cells of each colony. MaBChE nucleotide sequence in the isolated genomic DNA was detected by the PCR amplification using MaBChE specific oligonucleotides.

Example 7

Coexpression of a PRAD Peptide Together with Butyrlcholinesterase in Mammalian and Plant Cells Expressing BChE Enhances Tetrameric Forms of the Enzyme The principle of this invention is further demonstrated by the ability to enhance tetramerization of expressed monomeric butyrlcholinesterase expressed in mammalian and plant cells by the co-expression of a proline-rich attachment domain (PRAD).

Data suggest that for optimal detoxification activity by BChE, the tetrameric form of the enzyme is required. A heteromeric form of BChE is, formed by the attachment of the catalytic subunit to a triple helical collagen-like tail subunit. The function of the collagen-like tail is to anchor catalytic subunits to the basal lamina. The triple helical association of three collagen-like strands, ColQ, forms the tail. The PRAD of each strand can bind the catalytic subunit tetramer producing the asymmetric moieties.

The PRAD fragment was amplified using PfuTurbo DNA Polymerase and a pair of synthesized oligonucleotide primers, O-Pro#6 and O-Pro#8, and the amplified fragments were cloned into pCRII vector (Invitrogen). A plasmid vector of PRAD with FLAG sequence (PRAD-FLAG) at the carboxy-terminal in pCRII vector was also amplified using PfuTurbo DNA Polymerase and a pair of synthesized oligonucleotide primers, O-Pro#6 and O-Pro#7 and the amplified fragment was cloned into pCRII vector. The addition of FLAG at the carboxyterminal PRAD will allow the purification of MaBChE tetramer by passing the culture fluid over a FLAG-antibody containing column. The nucleotide sequence of both PRAD and PRAD-FLAG has been confirmed by commercial sequencing of the fragments in the vectors. The nucleotide sequence encoding PRAD and PRAD-FLAG fragments are excised from the corresponding vectors with appropriate restriction enzymes and cloned into pcDNA4 plasmid vector for mammalian cell expression, and pTRAkt plasmid vector for plant expression.

For the production of tetrameric BChE, CHO-K1 tranfected with pcDNA3.1-MaBChE and expressing high level of MaBChE is retransfected with pcDNA4-PRAD or pcDNA4-PRAD-FLAG. The transfected cells are selected by the addition of zeocine in the media at a concentration of 200 mg/liter for 2 weeks. The amount of tetrameric MChE relative to dimer and monomer are determined by northern blot of the media collected after 2 days secretion of BChE using anti-BChE antibody. If necessary, high ratio of tetramer producing cells are isolated by limiting dilution of the transfected cells.

Example 8

Cloning of MaBChE-534stop Encoding BChE Monomeric Molecules

A plasmid vector harboring truncated form of MaBChE which prevents tetramerization was made for the production of momomeric MaBChE production in mammalian cells. The DNA fragment lacking the sequence encoding the tertramerization domain was prepared by PCR amplification of MaBChE gene using PfuTurbo DNA Polymerase with a pair of oligonucleotide primers, O-Pro#11 and O-Pro#33. The resulted DNA fragment, MaBChE-534stop was cloned into an intermediate pCRII vector. The nucleotide sequence of the truncated MaBChE was confirmed by commercial sequencing. The MaBChE-534stop DNA fragment was excised from the pCRII vector with appropriate restriction enzymes and cloned into pcDNA (pcDNA3.1-MaBChE-534stop) for the expression in mammalian cells. For the expression in plant, the MaBChE-534stop fragment is cloned into pTRAkt.

Example 9

In vitro Post-translational Modification of Butyrlcholinesterase to Produce a Recombinant Protein with Properties Similar to the Native Form As previously noted, the native glycosylation profile of any effective nerve agent scavenger is essential for good in vivo stability and while many expression systems have been very successful in expressing functional non-gylcosylated proteins, they have been inadequate in terms of preserving the correct glycans on heavily glycosylated proteins such as BChE. Even though clever molecular engineering and other elegant manipulations of producer cells, animal or plants are largely overcoming these problems, they have often met with limited success to date because they are imperfect, time consuming and may sacrifice expression levels. An alternate and much more rapid technology is the sialylation of the expressed purified protein in vitro. The structures with exposed GlcNAc and/or Galactose with remodeling resulting in nearly quantitative coverage of all galactosyl residues by sialic acid. This technology has to date been use to successfully remodel >40 compounds and can results in an increase in the number of sialylation sites occupied from of 64% to 92%.

Example 10

The Ability of the OP-inhibited rBChEs to Undergo Spontaneous or Oxime-Induced Reactivation Due to rapid irreversible inhibition of OP-inhibited ChEs, reactivation of the enzyme scavenger is often virtually impossible. This is particularly the case following interaction with nerve agents such as soman which renders the enzyme non-reactivatable almost immediately. At a mechanistic level, the reaction between organophosphates and ChEs results in the creation of phosphylated enzyme complexes involving the active-center serine (S198 for BChE) followed by either spontaneous or induced regeneration of the active site. Reaction of OP with the BChE-esterase results in rapid cleavage of the alkoxy-O—P bond and the formation of P—O⁻ conjugates resulting in irreversible inhibition "aging" of some enzyme scavengers. Studies on aging of AChE have been shown to depend on the structure of the OP, enzyme source, pH, temperature and ionic strength of the solution. The aging process, characteristic of ChEs (in contrast to carboxylesterase) bioscavengers, has stimulated the generation of ChE mutants which are more easily reactivated than the wild type enzyme. For example, E202Q, an AChE mutant has been shown to be 2-3 times better in detoxifying sarin and soman, decreased the affinity of soman for AChE, slowed the reactivation of soman-inhibited AChE by HI-6 and decreased aging. In the presence of 2 mM of HI-6, the same amount of WT and E202Q AChE could detoxify 135- and 225~fold molar excess of soman respectively, indicating the superior properties of the mutant compared to the WT enzyme In the latter case, the reaction of oxime nucleophile with the phosphonylated enzyme leads to displacement of the phosphonyl group and restoration of normal activity. Thus, oximes act on the inactivated ChE rather than protect against OP inactivation itself. In this context, exogenously administered FBS AChE inhibited by the powerful anticholinesterase MEPQ has been shown shown to be reactivated in mice by an i.m. injection of TMB4 (1,1.trimethylene bis (4-hydroxyiminomethylpyridinium) permitting the reactivated enzyme to protect the mice against exposure to an additional dose of MEPQ.

Example 11

Cloning of E1970 BChE Mutant Gene with Enhanced Scavenging Ability

In an attempt to increase scavenging efficacy, mutants enzyme molecules can be created which exhibit reduced rates of inhibition following interaction with OP as well as a reduced rate of aging, thus allowing persistence of the active enzyme. In this context, an amino acid change, replacement of 197 glutamic acid to glutamine (E197Q), of hrBChE has shown better toxic agent scavenging activity. A plasmid vector harbouring the E197Q mutation in MaBChE (pcDNA3.1-MaBChE-E197Q) has been constructed by site-directed mutagenesis. First, E197Q point mutation containing oligonucleotides (O-Pro#49 and O-Pro#10) were synthesized from both strands of MaBChE gene in pcDNA3.1-MaBChE plasmid. Two fragments of MaBChE gene were PCR amplified using PfuTurbo DNA Polymerase and two pairs of primers. The 5'-fragment was amplified by O-Pro#11 and O-Pro#10 and the 3'-fragment by O-Pro#9 and O-Pro#12. The resulting DNA fragments were isolated from the reaction mix by PCR purification kit (Invitrogen). The amplified and purified 5'- and 3'-fragments were mixed and 5 thermal-cycles were performed in the reaction mix without primers to create the full length template. The resulted full length template containing E197Q mutation, then, diluted 100 to 1000 fold and was used as a template to amplify the E197Q MaBChE gene using PfuTurbo DNA Polymerase with P-Pro#11 and O-Pro#12. The amplified fragment was cloned into an intermediate pCRII vector and the nucleotide sequence was confirmed by commercial sequencing. The MaBChE-E197Q gene in pCRII vector was excised by appropriate restriction enzymes and cloned into pcDNA3.1 for the expression in mammalian cells.

The invention claimed is:

1. A method of treating a human for exposure to a neurotoxin which comprises administering by inhalation to the lungs of said human an effective amount of a bioscavenger molecule that detoxifies said neurotoxin, wherein said neurotoxin is a nerve agent or a pesticide, and wherein said bioscavenger molecule is a paraoxonase, an organophosphate hydrolase, an organophosphorous acid anhydrolase or a parathion hydrolase which enzymatically cleaves said neurotoxin.

2. The method of claim 1, which comprises administering by inhalation said bioscavenger molecule prior to exposure to said neurotoxin.

3. The method of claim 1, wherein said bioscavenger molecule is administered by inhalation after exposure to said neurotoxin.

4. The method of claim 1, wherein said neurotoxin is an organophosphate.

5. The method of claim 1, wherein said bioscavenger molecule is a human enzyme.

6. The method of claim 1, wherein said bioscavenger molecule is administered by inhalation in powder form.

7. The method of claim 1, wherein said bioscavenger molecule is administered by inhalation in liquid form.

8. The method of claim 4, wherein said organophosphate is selected from the group consisting of sarin (O-isopropyl-methylphosphonofluoridate), V X (ethyl-S-2-diisopropylaminoethyl-phosphano-thiolate), MEPQ (7-(methylethoxy-phosphinyloxy)-1-methylquinolinium iodide), soman (pinacolylmethyl-phosphonofluoridate), DFP (diisopylfluorophosphate paraoxon) malathion and parathion.

9. The method of claim 1, wherein said bioscavenger molecule is a native molecule.

10. The method of claim 1 wherein said bioscavenger molecule is a recombinant molecule.

11. The method of claim 10, wherein said recombinant molecule is produced in vitro in mammalian or insect cells.

12. The method of claim 10, wherein said recombinant molecule is glycosylated.

13. The method of claim 11, wherein said mammalian cells are Chinese Hamster Ovary (CRO) cells.

14. The method of claim 10, wherein said recombinant molecule is produced in vivo in a transgenic plant.

15. The method of claim 10, wherein said recombinant molecule is produced in vivo in a transgenic non-human animal.

16. The method of claim 1, which further comprises administering with said bioscavenger molecule, a permeation enhancer.

17. The method of claim 16, wherein said permeation enhancer is selected from the group consisting of oleic acid, dimethyl-b-cyclodextrin, citric acid and polyethylene glycol.

18. The method of claim 7, wherein said liquid form comprises an aerosol.

19. The method of claim 6, wherein said powder form comprises an aerosol.

20. The method of claim 12, wherein glycosylation comprises sialylation.

21. The method of claims 10, wherein said recombinant molecule is produced by a transient expression system.

* * * * *